US011351280B1

(12) United States Patent
White

(10) Patent No.: US 11,351,280 B1
(45) Date of Patent: Jun. 7, 2022

(54) APPARATUS AND METHOD FOR GLOVE SANITIZATION

(71) Applicant: Karen White, Fairview, OR (US)

(72) Inventor: Karen White, Fairview, OR (US)

( * ) Notice: Subject to any disclaimer, the term of this patent is extended or adjusted under 35 U.S.C. 154(b) by 0 days.

(21) Appl. No.: 17/514,480

(22) Filed: Oct. 29, 2021

(51) Int. Cl.
*A61L 2/10* (2006.01)

(52) U.S. Cl.
CPC .............. *A61L 2/10* (2013.01); *A61L 2202/11* (2013.01)

(58) Field of Classification Search
CPC ................................ A61L 2/10; A61L 2202/11
See application file for complete search history.

(56) References Cited

U.S. PATENT DOCUMENTS

| 11,007,292 B1* | 5/2021 | Grenon | G01J 1/429 |
| 11,224,107 B1* | 1/2022 | Avery | H05B 47/17 |
| 2013/0212900 A1* | 8/2013 | Stewart | A61L 2/16 34/275 |
| 2021/0338867 A1* | 11/2021 | Gibson | A61L 2/26 |

* cited by examiner

*Primary Examiner* — Sean E Conley

(57) ABSTRACT

A system and method for sanitizing the interior surface of gloves is provided. One embodiment comprises at least one ultra violet (UV) lamp, wherein the at least one UV lamp is sized and shaped to fit within a selected region within an interior of the glove, and wherein the least one UV lamp emits UV radiation at a predefined intensity for a predefined duration that kills at least one consisting of a virus, a bacteria, and a mold that resides on the interior surface of the selected region of the glove.

13 Claims, 5 Drawing Sheets

APPARATUS AND METHOD FOR GLOVE SANITIZATION

BACKGROUND OF THE INVENTION

Sterilization of surfaces is of interest in view of the heightened awareness of surface transmitted virus, bacteria, and/or mold. Such virus, bacteria or mold lingering on surfaces may potentially cause colds, flu, COVID-19, or other infectious disease to a person coming in contact with such contaminated surfaces.

Often, the surface of an object may be sterilized by cleaning with a solution having a sanitizing chemical. For example, countertops may be cleaned using a variety of readily available cleaning products.

Various sterilization devices have been devised to sterilize surfaces of objects using ultra violet (UV) radiation. A UV light source is used to direct UV light onto a surface of an object that is to be sterilized. The incident UV light kills viruses, bacteria and/or molds. For example, a container configured to enclose a smart phone and emit UV radiation within the container is available to sterilize smart phones.

One example object that cannot be readily sterilized is the interior surface of a glove. Washing a pair of gloves may be effective for sterilizing the interior of the gloves. However, washing is entirely unsatisfactory for leather gloves because such washing will damage the leather material of the gloves.

Accordingly, in the arts of sterilization of surfaces, there is a need in the arts for improved methods, apparatus, and systems for sterilizing the interior surfaces of gloves.

SUMMARY OF THE INVENTION

Embodiments of the glove sanitizing device system sanitize the interior surface of gloves. One embodiment comprises at least one ultra violet (UV) lamp, wherein the at least one UV lamp is sized and shaped to fit within a selected region within an interior of the glove, and wherein the least one UV lamp emits UV radiation at a predefined intensity for a predefined duration that kills at least one consisting of a virus, a bacteria, and a mold that resides on the interior surface of the selected region of the glove.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
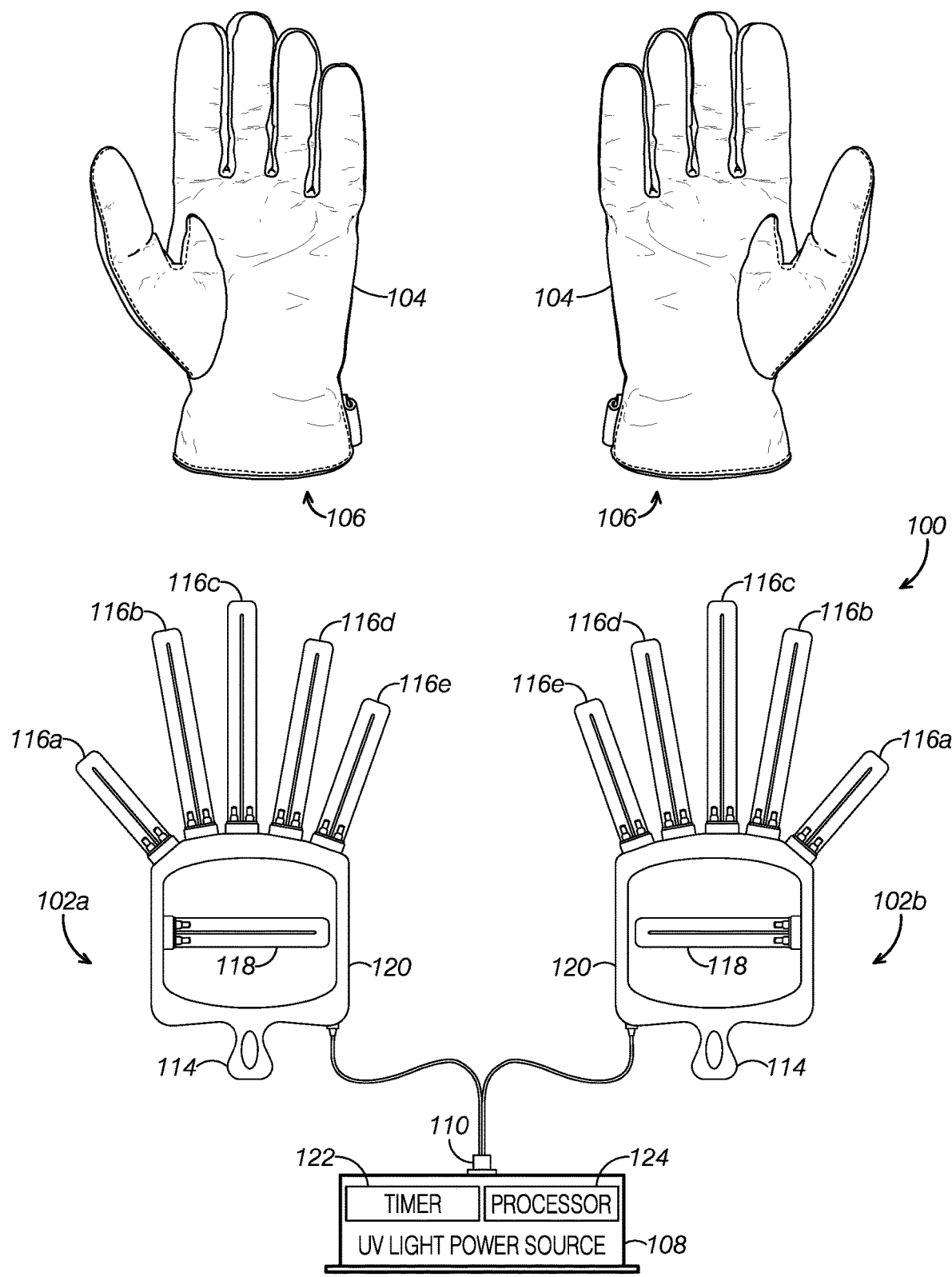
FIG. 1 is a diagram of an ultraviolet (UV) glove sanitizing device system.

FIG. 1 is a diagram of an ultraviolet (UV) glove sanitizing device system 100. Embodiments of the UV glove sanitizing device system 100 preferably comprises two UV glove sanitizing devices 102a, 102b (generically referred herein using reference numeral 102). Each UV glove sanitizing device 102 is configured to fit into the interior 106 of a glove 104. In particular, embodiments of the UV glove sanitizing device 102 have UV lamps that are configured to be inserted into selected region of the glove, such as the digit regions of the glove 104, wherein the interior surface of the digit regions are configured to cover a corresponding digit of the user's hand. Further, embodiments of the UV glove sanitizing device 102 have one or more UV lamps that are configured to be inserted into a palm region of the glove 104, wherein the interior surface of the palm region is configured to cover a palm and a top surface of the user's hand.

When the UV glove sanitizing device 102 emits UV radiation into the interior 106 of the glove 104, the interior surfaces of the glove 104 are sanitized. That is, virus, bacteria, or mold on the interior surfaces of the glove 104 are killed when one or more UV lamps emit UV radiation at a predefined intensity for a predefined duration onto the interior surface of the glove 104.

The disclosed systems and methods for sanitizing the interior surfaces of a glove 104 using embodiments of the UV glove sanitizing device system 100 will become better understood through review of the following detailed description in conjunction with the figures. The detailed description and figures provide examples of the various inventions described herein. Those skilled in the art will understand that the disclosed examples may be varied, modified, and altered without departing from the scope of the inventions described herein. Many variations are contemplated for different applications and design considerations, however, for the sake of brevity, each and every contemplated variation is not individually described in the following detailed description.

Throughout the following detailed description, a variety of examples for systems and methods for the UV glove sanitizing device system 100 are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components. "Secured to" means directly connected without intervening components.

Returning to FIG. 1, embodiments of the UV glove sanitizing device system 100 preferably comprise two UV glove sanitizing devices 102 so that each one of a pair of gloves 104 may be concurrently sanitized after a user has worn their gloves. Alternative embodiments may have one UV glove sanitizing device 102 so that individual gloves 104 can be sanitized one at a time. A plurality of UV glove sanitizing devices 102 may be used to concurrently sanitize a corresponding number of gloves 104.

The one or more UV glove sanitizing devices 102 are coupled to a suitable UV light power source 108 via a connector device 110. Any suitable UV light power source 108 may be used in the various embodiments. The connector device 110 may be any suitable adaptor that connects to a source of power that will actuate one or more UV lamps of a UV glove sanitizing device 102. For example, but not limited to, the connector device 110 may be a uniform serial bus (USB) connector configured to couple to a USB power supply 108. As another example, the connector device 110 may be an alternating current (AC) plug configured to receive power from a wall outlet or extension cord that is coupled to a legacy power grid. The connector device 110 may be configured to couple to a battery power supply 108, or may be configured to receive one or more batteries 108. Some embodiments may be configured to receive power from multiple different types of UV light power sources 108.

In an example embodiment, an optional branching wire connector 112 couples the UV light power source 108 to each of the UV glove sanitizing devices 102 or even a plurality of UV glove sanitizing devices 102. Alternatively, two separate wire connectors 112 may be used. Preferably, the wire connector 112 is made of an insulated flexible wire with sufficient length to permit the user to conveniently manipulate the UV glove sanitizing devices 102 while inserting the UV glove sanitizing device 102 into the interior 106 of the glove 104.

The user may grasp an optional protruding handle 114 of the UV glove sanitizing device 102 when inserting or retracting the UV glove sanitizing device 102 into/from a glove 104. The handle 104 may be of any suitable size, shape or form. Alternatively, some embodiments of the UV glove sanitizing device 102 may be secured to a stationary platform or the like. In such embodiments, the UV light power source 108 may be an integrated component of the platform.

In a preferred embodiment, the UV glove sanitizing device 102 comprises five UV digit lamps 116a-e (generically referred to as a UV digit lamp 116) and a UV palm lamp 118. The UV digit lamps 116 are configured to each be insertable into the interior of one of the digit regions (the four glove fingers and the glove thumb) of the glove 104.

The UV palm lamp 118 is configured to be inserted into the interior palm region of the glove 104. For purposes of this disclosure, the palm region also includes the top hand surface of the wearer's hand that is covered by the glove 104. When operating, the UV palm lamp concurrently sanitizes the palm region and the top hand surface region of the interior surface of the glove.

When the UV digit lamps 116 are energized while inserted into the digits of the glove 104, the predefined intensity of the emitted UV radiation is sufficient to kill any virus, bacteria, or mold that may be present on the interior surface of the glove digits. Similarly, when the UV palm lamp 118 is energized while inserted into the palm region of the glove 104, the predefined intensity of the emitted UV radiation is sufficient to kill any virus, bacteria, or mold of interest that may be present in the interior palm region of the glove 104.

The proximal ends of the UV digit lamps 116 and the UV palm lamp 118 are preferably secured to a body member 120. The protruding handle 114 may be secured to the body member 120 or may be an integrated component of the body member 120.

Suitable wire-based electrical connectors (not shown) are embedded within the body member 120 to electrically couple the UV lamps 116, 118 to the UV light power source 108. Preferably, the UV lamps 116, 118 use plug-in type connectors to removably couple to the body member 120. Accordingly, a failed one of the UV lamps 116, 118 can be easily replaced by the user.

Preferably, the body member 120 is made of a flexible material, or semi-flexible material to permit orientation of the UV digit lamps 116 (bending and flexing) when the user is inserting the UV glove sanitizing device 102 into the interior 106 of the glove 104. Alternatively, the body member 120 may be rigid if the UV digit lamps 116 are oriented in a predefined manner so that UV digit lamps 116 can be inserted into the digits of the glove 104.

One skilled in the art appreciates that the effectiveness of killing virus, bacteria, and/or mold depends upon (1) the intensity and amount of the emitted UV radiation, (2) distance of the surface from the UV radiation source, and (3) the duration that the UV radiation is omitted. These three design parameters may be varied in a predefined manner in the various embodiments so that the UV glove sanitizing device system 100 has the desired effect of sterilizing the interior 106 of a glove 104.

In the example embodiment of FIG. 1, the UV lamps 116 each may have a different length to correspond to the length of the corresponding glove digit. For example, one skilled in the art appreciates that the length of a typical thumb is less that the length of the typical index finger. Accordingly, the length of the UV digit lamp 116a for the thumb digit is preferably less than the length of the UV digit lamp 116c of the index finger digit of the glove 104. By employing UV lamps 116 that correspond to the length of its corresponding glove digit, the distal ends of the UV lamps 116 will preferably protrude up into the farthest extent of the glove digits. Accordingly, when UV radiation is emitted from the UV lamps 116, the interior surfaces at the tip of the glove digits will be sanitized.

One skilled in the art appreciates that gloves come in many different sizes and forms. For example, small gloves may be worn by children, an intermediate size glove may be worn by women or young adults, and a large glove may be worn by large men.

One skilled in the art appreciates that the palm region of the glove 104 is larger than any of the individual digits or thumb of the glove 104. Accordingly, the UV palm lamp 118 may be larger than the UV digit lamps 116 so as to emit a suitable greater amount of UV radiation than the UV digit lamps 116 so as to sterilize the larger interior surface area of the glove palm region. Alternatively, or additionally, the UV palm lamp 118 may be configured to emit a higher UV radiation intensity than the UV digit lamps 116 to sterilize the larger area of the glove palm region. Alternatively, or additionally, the duration of energization of the UV palm lamp 118 may be longer than the duration of the UV digit lamps 116 to sterilize the larger area of the glove palm region.

In some embodiments, an optional timer 122 may be used to automatically shut off the UV glove sanitizing device system 100 at the conclusion of a sanitization process. A mechanical timer 122 or a processor-based timer 122 may be used.

In a processor-based embodiment, a processor 124 may be used to control individual UV lamps 116, 118 during a sterilization process. Duration and/or intensity of UV radiation emission may be controlled by the processor 124. The processor 124 may even be configured to individually control the UV lamps 116, 118. In some embodiments, the length, size, amount and/or intensity of UV radiation emission may be different in one or more of the UV digit lamps 116 from the other UV palm lamps 118 and/or the UV digit lamps 116.

FIG. 1 conceptually illustrates the timer 122 and the processor 124 as being integrated components of the UV light power source 108. In other embodiments, the timer 122 and/or the processor may be separate from the UV light power source 108 and/or from each other.

Figure 2:
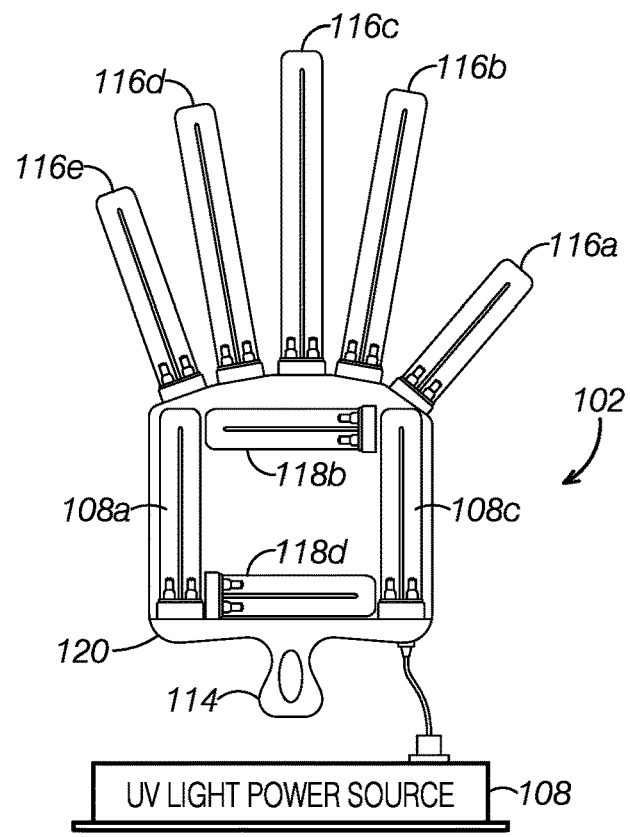
FIG. 2 is a diagram of a UV glove sanitizing device system employing a plurality of UV palm lamps.

FIG. 2 is a diagram of a UV glove sanitizing device system employing a plurality of UV palm lamps 118*a-d*. The UV palm lamps 118*a-d* are arranged so as to extend into the farthest extents of the palm region of the 104 (FIG. 1). That is, the plurality of palm lamps 118 cooperatively act to spread open the interior palm region of the glove 104 to expose all of, or substantially all of, the interior surface of the palm region to UV radiation emitted by the plurality of UV palm lamps 118. Any suitable number of UV palm lamps 118 may be used in the various embodiments.

Figure 3:
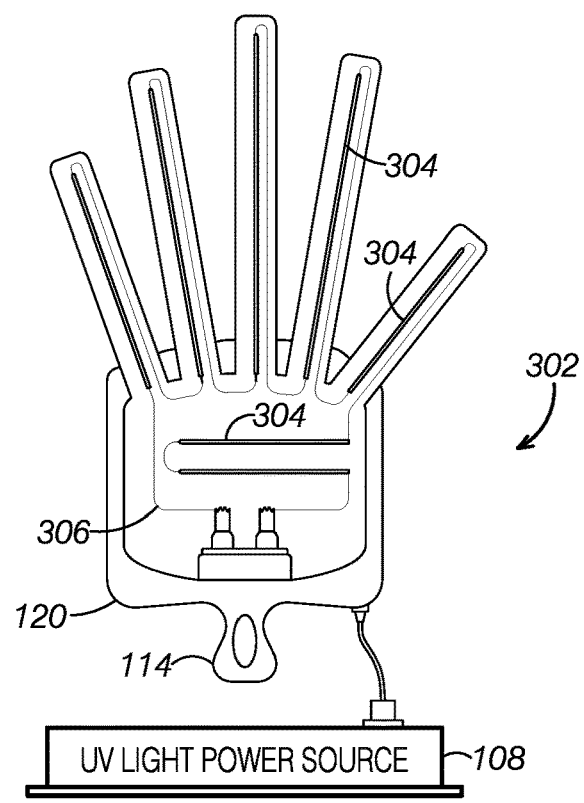
FIG. 3 is a diagram of a UV glove sanitizing device system employing a single UV lamp.

FIG. 3 is a diagram of a UV glove sanitizing device system employing a single UV lamp 302. One skilled in the art appreciates that UV lamps may be fabricated in a variety of sizes and/or shapes. Accordingly, FIG. 3 conceptually illustrates a single lamp embodiment wherein the exterior surfaces of the UV glove sanitizing device 102 correspond to the digits and the interior palm region of the glove 104. Here, a plurality of UV light emitting filaments 304 are connected in series via a suitable connector 306 that received power from the UV light power source 108. The filaments 304 may be light emitting diode (LED) filaments in some embodiments.

Other forms of single UV lamps may be used by alternative embodiments of the UV glove sanitizing device 102. All such variations are intended to be included within the scope of this disclosure and to be protected by the accompanying claims.

Figure 4:
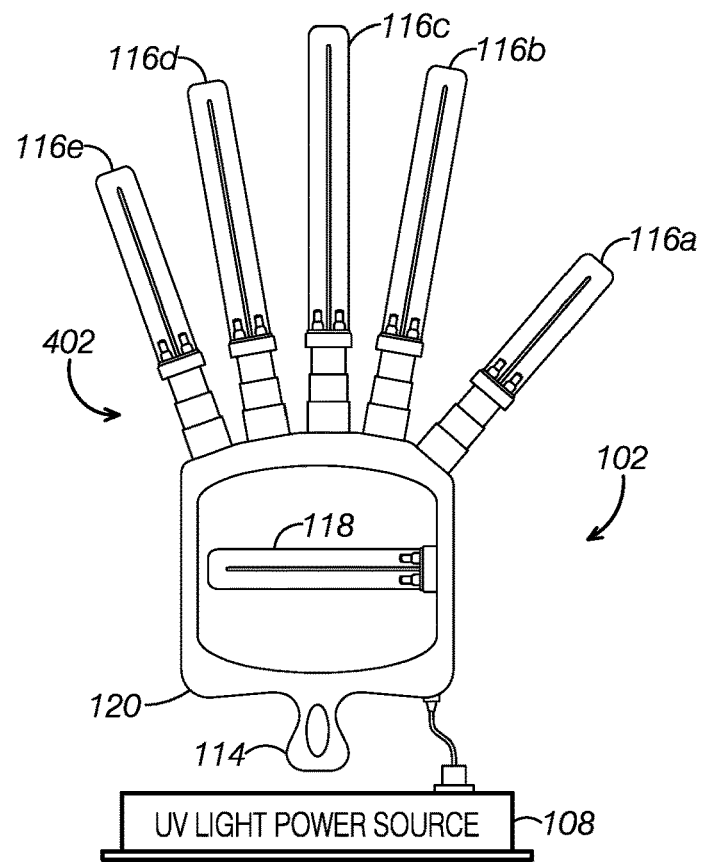
FIG. 4 is a diagram of a UV glove sanitizing device system employing a plurality of extension members disposed at the proximal end of each of the UV digit lamps.

FIG. 4 is a diagram of a UV glove sanitizing device system 100 employing a plurality of extension members 402 disposed at the proximal end of each of the UV digit lamps 116. The extension member 402 is configured to permit the user to adjust the extent of each of the UV digit lamps 116 to a desired length. Accordingly, a single UV glove sanitizing device 102 may be configured as needed by the user to fit the UV glove sanitizing device 102 to the different sizes and shapes of their gloves 104 (FIG. 1).

For convenience, the extension members 402 are illustrated as telescoping devices. Other types of length-adjustable extension members 402 may be used in other embodiments. All such variations are intended to be included within the scope of this disclosure and to be protected by the accompanying claims.

In practice, the extension members 402 are thin enough to reduce significant blockage from the emitted UV light, thereby permitting the emitted UV radiation from the UV digit lamps 116 and or the UV palm lamp 118 to sterilize the interior of the digits of the glove 104 proximate to the extension members 402. Alternatively, or additionally, a clear plastic or acrylic material may be used for the extension members 402 to facilitate transmission of the UV radiation to sterilize the interior of the digits of the glove 104 proximate to the extension members 402. Some embodiments may even include small UV digit lamps 116 as part of an extension member 402. All such variations are intended to be included within the scope of this disclosure and to be protected by the accompanying claims.

Figure 5:
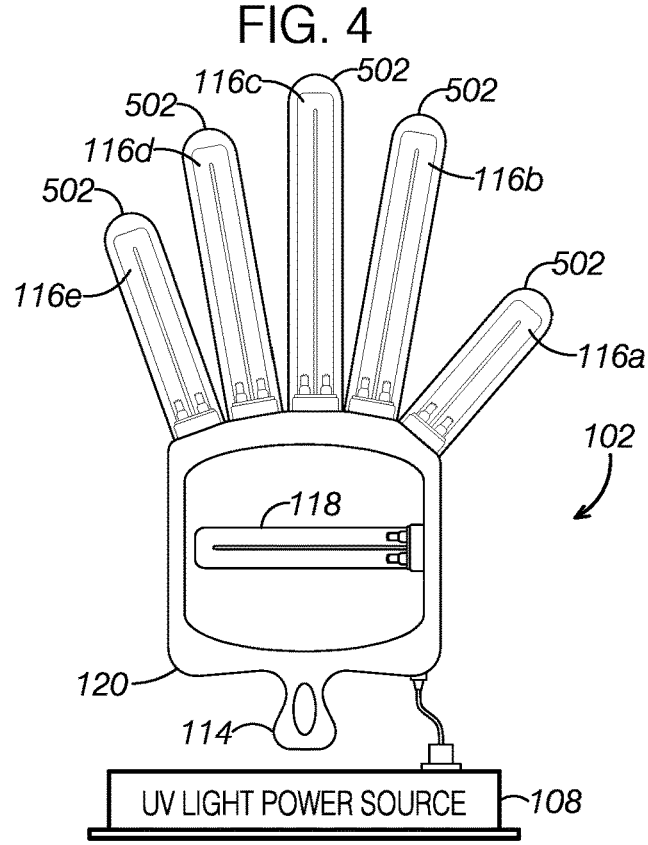
FIG. 5 is a diagram of a UV glove sanitizing device system employing a plurality of UV translucent protective shells with the UV digit lamps inserted therein for protection.

FIG. 5 is a diagram of a UV glove sanitizing device system 100 employing a plurality of UV translucent protective shells 502 protectively covering the UV digit lamps 116. Further, the translucent protective shells 502 expand the glove digit region to a fuller extent to facilitate sterilization of the interior surface of the glove digit. The UV translucent protective shells 502 have a hollow cavity that receives the UV digit lamps 116. The UV translucent protective shells 502 are preferably removably fixed to the body member 120 so that replacement UV digit lamps 116 can be installed as needed. In the various embodiments, the UV translucent protective shells 502 may be made of glass, plastic, acrylic, etc. The translucent protective shells 502, or portions thereof, may be made of any suitable flexible, semi-flexible, semi-rigid, or rigid UV translucent material. All such embodiments are intended to be included within the scope of this disclosure and to be protected by the accompanying claims.

Figure 6:
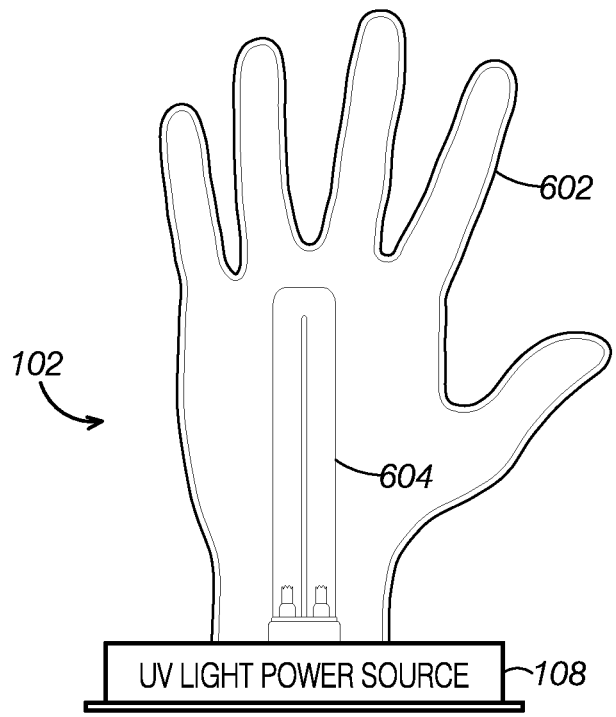
FIG. 6 is a diagram of a UV glove sanitizing device system employing a UV translucent shell that is configured to be inserted into the interior of a glove.

FIG. 6 is a diagram of a UV glove sanitizing device system 100 employing a UV translucent shell 602 that is configured to be inserted into the interior 106 of a glove 104 (FIG. 1). The UV translucent shell 602 is shaped like, or similar to, a person's hand that fits into the interior 106 of the glove. The UV translucent shell 602 may be made of glass, plastic, acrylic, etc. that permits transmission of the UV radiation through the UV translucent shell 602 and onto the interior surface of the glove 104. The UV translucent shell 602 may have a hollow cavity or may be solid. The UV translucent shell 602, or portions thereof, may be made of any suitable flexible, semi-flexible, semi-rigid, or rigid UV translucent material.

In an example embodiment conceptually illustrated in FIG. 6, a single UV lamp 604 is arranged within the interior of the UV translucent shell 602. Any suitable number of UV lamps, including the example UV digit lamps 116 and/or UV palm lamp 118 (FIGS. 1-5), may be used in the various embodiments. All such embodiments are intended to be included within the scope of this disclosure and to be protected by the accompanying claims.

In the conceptual example embodiment of FIG. 6, the UV glove sanitizing device 102 is mounted to the UV light power source 108 or another stationary member. In some embodiments, the body member 120 and/or the handle 114 may optionally be included within the interior of the UV translucent shell 602 so that the tethered UV glove sanitizing device 102 can be manipulated by the user. In other embodiments, the body member 120 and/or the handle 114 may be an integrated component of the UV translucent shell 602. All such embodiments are intended to be included within the scope of this disclosure and to be protected by the accompanying claims.

Figure 7:
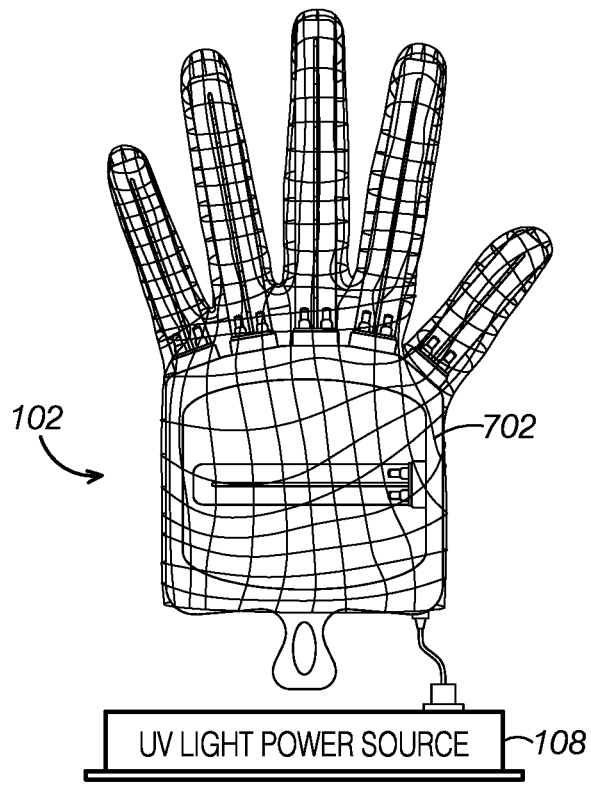
FIG. 7 is a diagram of a UV glove sanitizing device system employing a mesh member that is configured to be inserted into the interior of a glove so that the interior of the glove is expanded when the UV glove sanitizing device is inserted into the glove.

FIG. 7 is a diagram of a UV glove sanitizing device system 100 employing a mesh member 702 that is configured to be inserted into the interior 106 of a glove 104 (FIG. 1) so that the interior 106 of the glove 104 is expanded when the UV glove sanitizing device 102 is inserted into the glove 104. By expanding the interior 106 of the glove 104 using the mesh member 702, more of the interior surface of the glove 104 will be exposed to the emitted UV radiation.

The mesh member 702 may be made of metal, plastic, acrylic wire or the like. In some embodiments, the mesh member 702 may be made of any suitable flexible, semi-flexible, semi-rigid, or rigid material. Optionally, the material of the mesh member 702 may be UV translucent. In the illustrated embodiment, the mesh member 702 encompasses the palm region and all of the digit regions of the glove 104. In alternative embodiments, the mesh member 702 encompasses only the palm region of the glove 104. All such embodiments are intended to be included within the scope of this disclosure and to be protected by the accompanying claims.

Figure 8:
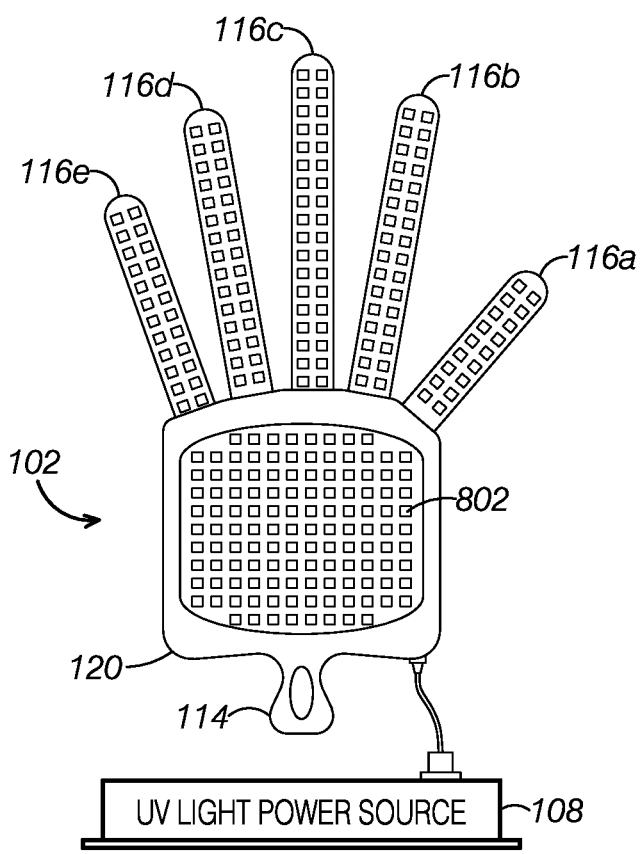
FIG. 8 is a diagram of a UV glove sanitizing device system employing a plurality of UV emitting diodes disposed on the digits and palm region of the UV glove sanitizing device.

FIG. 8 is a diagram of a UV glove sanitizing device system 100 employing an array of UV light emitting diodes 802 (conceptually illustrated as small squares of substrate forming a diode chip) disposed on the surfaces of the digits and palm region of the UV glove sanitizing device 102. In such embodiments, the body member 120 may be formed with a shape and size that corresponds to a glove 104 (FIG. 1), thus having digits and a palm region corresponding to the interior of the glove 104. The UV light emitting diodes 802 may then be fabricated onto the outside surface of the body member 120. Any UV diode now known or later developed is intended to be included within the scope of this disclosure and to be protected by the accompanying claims.

One skilled in the art appreciates that mittens are a form of glove 104, and may come in many different sizes. Mittens employ a single area that receives all of the user's four fingers, and a separate area for the thumb. Accordingly, embodiments of the UV glove sanitizing device system 100 may employ different sized UV glove sanitizing devices 102 that may be used to sanitize the interior surfaces of mittens.

Some UV glove sanitizing devices 102 that are used for gloves may be suitable for insertion into a mitten. Once inserted, the plurality of UV digit lamps 116 will emit UV radiation that sanitized the surface of the mitten that receives the user's four fingers. In an alternative embodiment, a single larger UV digit lamp 116 may be configured to be inserted into the region of the mitten that receives the user's four fingers. All such embodiments are intended to be within the scope of this disclosure and to be protected by the accompanying claims.

It should be emphasized that the above-described embodiments of the UV glove sanitizing device system 100 are merely possible examples of implementations of the invention. Many variations and modifications may be made to the above-described embodiments. All such modifications and variations are intended to be included herein within the scope of this disclosure and protected by the following claims.

Furthermore, the disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower, or equal in scope to the original claims, are to be considered within the subject matter of the inventions described herein.

Therefore, having thus described the invention, at least the following is claimed:

1. A ultra violet (UV) glove sanitizing device configured to sanitize an interior surface of a glove, comprising: at least one UV lamp, wherein the at least one UV lamp is sized and shaped to fit within a selected region within an interior of the glove, wherein the least one UV lamp is a first UV digit lamp of a group of at least five UV digit lamps, and wherein each one of the at least five UV digit lamps are configured to be inserted into a corresponding digit of the glove, and wherein the least one UV lamp emits UV radiation at a predefined intensity for a predefined duration that kills at least one consisting of a virus, a bacteria, and a mold that resides on the Interior surface of the selected region of the glove, further comprising an extension member secured to a proximal end of one of the at least five UV digit lamps, wherein the extension member is configured to permit adjustment of the one of the at least five UV digit lamps to a desired length so that the UV glove sanitizing device can be used with different glove sizes.

2. The UV glove sanitizing device of claim 1, wherein the interior surface of the selected region of the glove is an interior surface of a palm region that is configured to cover a palm of a hand of a user and a top hand surface of the user while wearing the glove, wherein the least one UV lamp is a UV palm lamp configured to be inserted into the palm region of the glove, and wherein the UV palm lamp concurrently sanitizes the palm region and the top hand surface region of the interior surface of the glove.

3. The UV glove sanitizing device of claim 2, wherein the UV palm lamp is a first UV palm lamp of a plurality of UV palm lamps, and wherein the plurality of palm lamps cooperatively open the palm regions to expose the extents of the interior surface of the palm region to UV radiation emitted by the plurality of UV palm lamps.

4. The UV glove sanitizing device of claim 1, wherein the interior surface of the selected region of the glove is an interior surface of a digit region that is configured to cover a digit a hand of a user while wearing the glove, wherein the first UV digit lamp sanitizes the digit region of the interior surface of the glove.

5. The UV glove sanitizing device of claim 4, wherein the digit region that is configured to cover the digit of the hand of the user while wearing the glove is a glove finger.

6. The UV glove sanitizing device of claim 4, wherein the digit region that is configured to cover the digit of the hand of the user while wearing the glove is a glove thumb.

7. The UV glove sanitizing device of claim 1, further comprising: a sixth UV lamp configured to be inserted into a palm region of the glove, wherein the sixth UV lamp concurrently sanitizes the palm region and the top hand surface region of the interior surface of the glove.

8. The UV glove sanitizing device of claim 1, further comprising: a translucent protective shell protectively covering at least one of the at least five UV lamps, wherein the translucent protective shell expands the digit of the glove to facilitate sterilization of an interior surface of the digit of the glove.

9. The UV glove sanitizing device of claim 1, further comprising: a body member, wherein the body member is secured to a proximal end of each one of the at least five UV digit lamps.

10. The UV glove sanitizing device of claim 9, wherein the at least five UV digit lamps are removably secured to the body member using a plug-in connector.

11. The UV glove sanitizing device of claim 9, wherein the body member is made of a flexible material that permits orientation of the at least five UV digit lamps when a user is inserting the UV glove sanitizing device into the interior of the glove.

12. The UV glove sanitizing device of claim 1, further comprising: a mesh member configured to be inserted into the interior of the glove, wherein the interior of the glove is expanded by the mesh member when the UV glove sanitizing device is inserted into the glove.

13. The UV glove sanitizing device of claim 1, further comprising: a UV translucent shell shaped like a hand that fits into the glove, wherein the UV translucent shell permits transmission of the UV radiation generated by the UV lamp through the UV translucent shell and onto the interior surface of the glove.

* * * * *